United States Patent
Thomas et al.

(10) Patent No.: US 10,669,591 B2
(45) Date of Patent: *Jun. 2, 2020

(54) **SELECTIVE DETECTION OF *HAEMOPHILUS INFLUENZAE***

(71) Applicant: THE GOVERNMENT OF THE UNITED STATES OF AMERICA AS REPRESENTED BY THE SECRETARY OF THE DEPARTMENT OF HEALTH AND HUMAN SERVICES, Rockville, MD (US)

(72) Inventors: Jennifer Thomas, Atlanta, GA (US); Xin Wang, Liburn, GA (US); Cynthia Hatcher, Atlanta, GA (US); Raydel Anderson, Lawrenceville, GA (US); Mary Jordan Theodore, Atlanta, GA (US); Leonard W. Mayer, Decatur, GA (US)

(73) Assignee: THE GOVERNMENT OF THE UNITED STATES OF AMERICA AS REPRESENTED BY THE SECRETARY OF THE DEPARTMENT OF HEALTH AND HUMAN SERVICES, Rockville, MD (US)

( * ) Notice: Subject to any disclaimer, the term of this patent is extended or adjusted under 35 U.S.C. 154(b) by 308 days.

This patent is subject to a terminal disclaimer.

(21) Appl. No.: 15/420,819

(22) Filed: Jan. 31, 2017

(65) Prior Publication Data

US 2017/0145479 A1 May 25, 2017

Related U.S. Application Data

(62) Division of application No. 13/996,913, filed as application No. PCT/US2012/022753 on Jan. 26, 2012, now Pat. No. 9,593,385.

(60) Provisional application No. 61/436,535, filed on Jan. 26, 2011.

(51) Int. Cl.
| | |
|---|---|
| *C12Q 1/689* | (2018.01) |
| *C12P 19/34* | (2006.01) |
| *C12Q 1/70* | (2006.01) |

(52) U.S. Cl.
CPC ............ *C12Q 1/689* (2013.01); *C12Q 1/701* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,858,677 A | 1/1999 | Forsgren | |
| 7,553,626 B2 | 6/2009 | Oh et al. | |
| 9,593,385 B2 | 3/2017 | Thomas et al. | |
| 2008/0305472 A1 | 12/2008 | Seki et al. | |
| 2009/0286239 A1 | 11/2009 | Seki et al. | |
| 2010/0068715 A1 | 3/2010 | Luyten et al. | |
| 2017/0145480 A1 | 5/2017 | Thomas et al. | |

OTHER PUBLICATIONS

Nakhjavani et al., "Detection of Haemophilus Influenzae Type B in Cerebrospinal Fluid of Suspected Children with Meningitis by PCR," Medical Journal of the Islamic Republic of Iran, vol. 19, No. 2, pp. 181-184. (Year: 2005).*
Marty et al., "Detection of Haemophilus influenzae Type b by Real-Time PCR," Journal of Clinical Microbiology, August., vol. 42, No. 8, pp. 3813-3815. (Year: 2004).*
GenBank Accession No. X90497 [retrieved on Apr. 1, 2019, publicly available 1998, retrieved from:https://www.ncbi.nlm.nih.gov/nucleotide/X90497.1?report=genbank&log$=nuclalign&blast_rank=1&RID=9WZYVNGD114] (Year: 1998).*
Falla et al., "PCR for Capsular Typing of Haemophilus influenzae," Journal of Clinical Microbiology, October, vol. 32, No. 10, pp. 2382-2386. (Year: 1994).*
Schweiger et al. (2000) J. Clin. Microbiol. vol. 38 No. 4: pp. 1552-1558.
Duim et al. (1997) Gene 191: 57-60.
Gou-Zhong, Tian et al., "Detection of Haemophilus Influenzae by Multiplex Polymerase Chain Reaction", Chin J Epidemiol, vol. 29, No. 8, Aug. 2008.
Wroblewski, D. et al., "Molcular and Cellular Probes," vol. 27 2 :86-89 2013.
Extended European Search Report for co-pending application No. EP12740015.8 dated May 21, 2015.
Schouls, et al. (2008) BMC Microbiology vol. 8:35 doi:10.1186/1471-2180/8/35.
Buck, et al. (1999) Biotechniques vol. 27: 528-536.
Marty, et al. (2004) J. Clin. Microbiol. vol. 42 No. 8 pp. 3813-3815.
Satola, et al. (2003) Infec. and Immunity vol. 71: No. 6 pp. 3639-3644.
Wang, X. et al., "C-170. Protein D Gene as a Target for Detection of *Haemophilus influenzae*," Abstracts of the General Meeting of the American Society for Microbiology, 109:130, May 19, 2009.

(Continued)

*Primary Examiner* — Young J Kim
(74) *Attorney, Agent, or Firm* — Kilpatrick Townsend & Stockton LLP

(57) ABSTRACT

A process for detecting *Haemophilus influenzae* nucleic acid in a sample includes producing an amplification product by amplifying a *Haemophilus influenzae* nucleotide sequence and measuring the amplification product to detect *Haemophilus influenzae* in the sample. Some embodiments allow direct serotype determination in a single step assay. Also provided are reagents and methods for detecting and distinguishing *Haemophilus influenzae* from other infectious agents. A kit is provided for detecting and quantifying *Haemophilus influenzae* in a sample.

19 Claims, 1 Drawing Sheet

Specification includes a Sequence Listing.

(56) References Cited

OTHER PUBLICATIONS

Maaroufi, Y et al., "Real-Time PCR for Determining Capsular Serotypes of *Haemophilus influenzae*," J. Clin. Microbial., 45(7): 2305-2308, May 16, 2007.
Abdeldaim, G. et al., "Detection of Haemophilus influenzae in repiratory secretions from pneumonia patients by quantitative real-time polymerase chain reaction," *Diagnostic Microbiology and Infectious Diseases*, 64(4): 366-373, (2009).
Naoko, C. et al., "Rapid detection of eight causative pathogens for the diagnosis of bacterial meningitis by real-time PCR," *J Infect Chemother*, 15:92-98 (2009).
Nakamura, S. et al., "Multiplex realOtime polymerase chain reaction for rapid detection of β-lactamase-negative, ampicillin-resistant Haemophilus influenzae," *Microbiology and Infectious Disease*, 64 (2009) pp. 64-69.
Wang, X. et al., "Dection of bacterial pathogens in Mongolia meningitis surveillance with a new real-time PCR assay to detect *Haemophilus influenzae*," *International Journal of Medical Microbiology*, 301 (2011) 303-309.
Wiertsema, S. et al., "Predominance of nontypeable *Haemophilus iinfluenzae* in children with otitis media following introduction of a 3 pneuococcal conjugate vaccine schedule," *Vaccine* 29 (2011) 5163-5170.
Supplementary Extended European Search Report issued by the European Patent Office dated Dec. 1, 2014 for co-pending application No. EP12740015.8.
Nakhjavani, F.A. et al., "Detection of Haemophilus Influenzae Type B in Cerebrospinal Fluid Of Suspected Children With Meningitis by PCR", MedicalJournal ofthe IslamicRepublicof Iran, Aug. 2005, vol. 19, No. 2, pp. 181-184.
Maaroufi, et al. (2007) J. of Clinical Microbiology vol. 45 No. 7 pp. 2305-2308.
Database:GenBank, "Haemophilus influenza serotype a capsulation locus region II DNA" Accesion No. Z37516.2, May 17, 2000, 1 pages.
Office Action from related Canadian Application No. 2822953, dated Oct. 30, 2017, 5 pages.
Office Action from related European Application No. 12740015.8, dated Dec. 19, 2016, 6 pages.
Examination Report from related Indian Application No. 5571/DELNP/2013, dated Aug. 28, 2018, 7 pages.
Office Action from related U.S. Appl. No. 15/420,836 dated Oct. 15, 2018, 6 pages.
Office Action from related U.S. Appl. No. 13/996,813 dated Feb. 12, 2015, 10 pages.
Office Action from related U.S. Appl. No. 13/996,813 dated Apr. 24, 2015, 30 pages.
Office Action from related U.S. Appl. No. 13/996,813 dated Aug. 6, 2015, 40 pages.
Office Action from related U.S. Appl. No. 13/996,813 dated Apr. 7, 2016, 15 pages.
Office Action from related U.S. Appl. No. 13/996,813 dated Aug. 15, 2016, 23 pages.
Notice of Allowance from related U.S. Appl. No. 13/996,813 dated Oct. 31, 2016, 16 pages.
Di Trani, et al., "A Sensitive One-Step Real-time PCR for Detection of Avian Influenza Viruses Using a MGB Probe an Internal Positive Control", BMC Infectious Diseases, vol. 6, No. 87, May 2006.
Non-Final Office Action dated U.S. Appl. No. 15/420,836, dated Apr. 15, 2019, 27 pages.
Final Office Action from related U.S. Appl. No. 15/420,836 dated Oct. 17, 2019, 35 pages.
Notice of Allowance from related U.S. Appl. No. 15/420,836 dated Feb. 7, 2020, 16 pages.

* cited by examiner

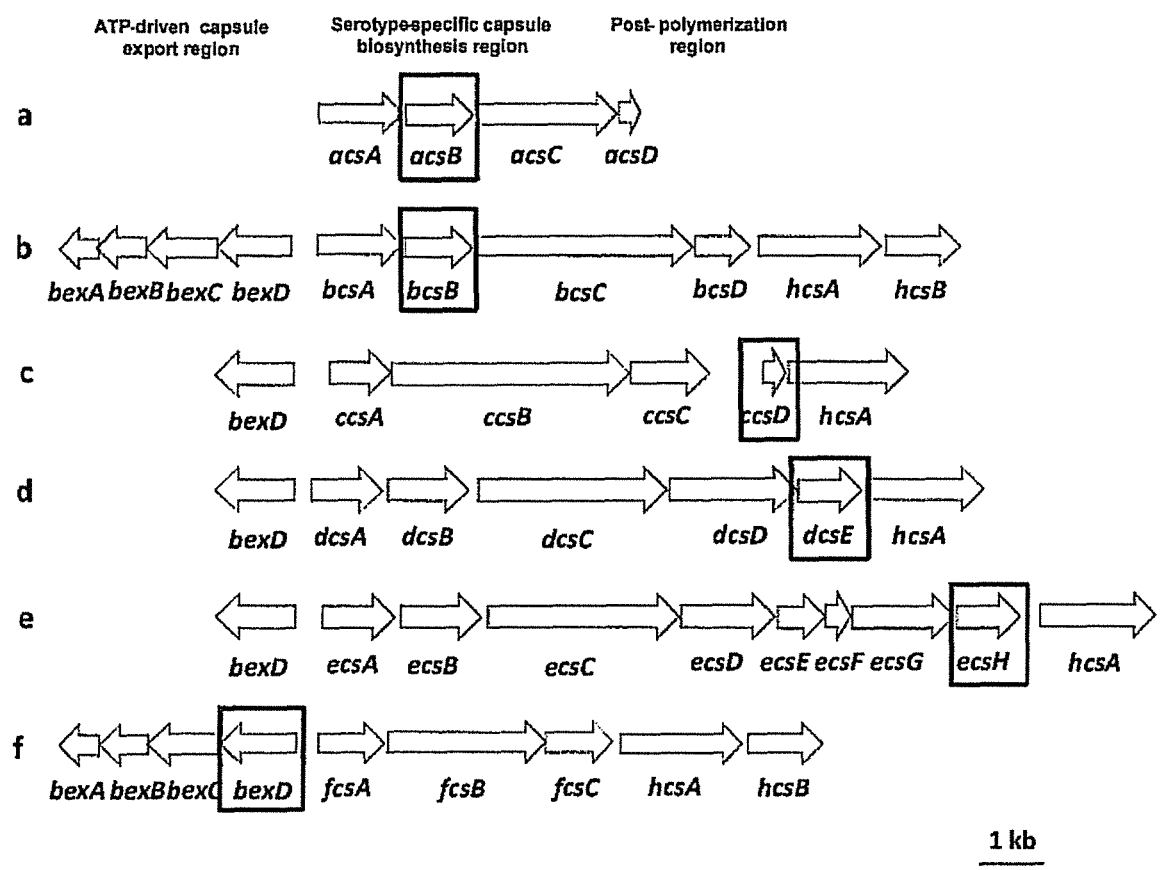

SEQUENCE LISTING

<160> NUMBER OF SEQ ID NOS: 30

<210> SEQ ID NO 1
<211> LENGTH: 19
<212> TYPE: DNA
<213> ORGANISM: Haemophilus influenzae

<400> SEQUENCE: 1
ggtctgcggt gtcctgtgt                                                    19

<210> SEQ ID NO 2
<211> LENGTH: 22
<212> TYPE: DNA
<213> ORGANISM: Haemophilus influenzae

<400> SEQUENCE: 2
ccggtcatct tttatgctcc aa                                                22

<210> SEQ ID NO 3
<211> LENGTH: 29
<212> TYPE: DNA
<213> ORGANISM: Haemophilus influenzae

<400> SEQUENCE: 3
taattttctt gctcaatacc gccttccca                                         29

<210> SEQ ID NO 4
<211> LENGTH: 26
<212> TYPE: DNA
<213> ORGANISM: Haemophilus influenzae

<400> SEQUENCE: 4
tgatgcattg aaagaaggtg taattt                                            26

<210> SEQ ID NO 5
<211> LENGTH: 25
<212> TYPE: DNA
<213> ORGANISM: Haemophilus influenzae

<400> SEQUENCE: 5
cctgcggtaa taacatgatc ataaa                                             25

<210> SEQ ID NO 6
<211> LENGTH: 31
<212> TYPE: DNA
<213> ORGANISM: Haemophilus influenzae

<400> SEQUENCE: 6
tgtcgtgcag tagcaaaccg taaccttact c                                      31

<210> SEQ ID NO 7
<211> LENGTH: 24
<212> TYPE: DNA
<213> ORGANISM: Haemophilus influenzae

<400> SEQUENCE: 7
cattggtgat ggttcagtta ttgg                                              24

<210> SEQ ID NO 8
<211> LENGTH: 22
<212> TYPE: DNA
<213> ORGANISM: Haemophilus influenzae

<400> SEQUENCE: 8
tacagcattc agcaataatg gg                                              22

<210> SEQ ID NO 9
<211> LENGTH: 24
<212> TYPE: DNA
<213> ORGANISM: Haemophilus influenzae

<400> SEQUENCE: 9
attgcatcgc cgcaggagtt cccg                                            24

<210> SEQ ID NO 10
<211> LENGTH: 23
<212> TYPE: DNA
<213> ORGANISM: Haemophilus influenzae

<400> SEQUENCE: 10
cctaaaatac ggacctagtg cac                                             23

<210> SEQ ID NO 11
<211> LENGTH: 22
<212> TYPE: DNA
<213> ORGANISM: Haemophilus influenzae

<400> SEQUENCE: 11
ccgatgagac caagtatggt ta                                              22

<210> SEQ ID NO 12
<211> LENGTH: 23
<212> TYPE: DNA
<213> ORGANISM: Haemophilus influenzae

<400> SEQUENCE: 12
aacgagctag agctggtgct gaa                                             23

<210> SEQ ID NO 13
<211> LENGTH: 23
<212> TYPE: DNA
<213> ORGANISM: Haemophilus influenzae

<400> SEQUENCE: 13
actaaaatat ggcccaaacc cac                                             23

<210> SEQ ID NO 14
<211> LENGTH: 22
<212> TYPE: DNA
<213> ORGANISM: Haemophilus influenzae

<400> SEQUENCE: 14
ccgatgagcc caagtatgat ga                                              22

<210> SEQ ID NO 15
<211> LENGTH: 23
<212> TYPE: DNA
<213> ORGANISM: Haemophilus influenzae

<400> SEQUENCE: 15
aacgagcaaa agccggtgcg gat                                             23

<210> SEQ ID NO 16
<211> LENGTH: 21
<212> TYPE: DNA
<213> ORGANISM: Haemophilus influenzae

<400> SEQUENCE: 16
ccctgaaaag cgttgactttt g                                             21

<210> SEQ ID NO 17
<211> LENGTH: 23
<212> TYPE: DNA
<213> ORGANISM: Haemophilus influenzae

<400> SEQUENCE: 17
ccaacttcag gaccaagtca ttc                                            23

<210> SEQ ID NO 18
<211> LENGTH: 29
<212> TYPE: DNA
<213> ORGANISM: Haemophilus influenzae

<400> SEQUENCE: 18
tgctgctaac tcagatgcat cagctcctt                                      29

<210> SEQ ID NO 19
<211> LENGTH: 27
<212> TYPE: DNA
<213> ORGANISM: Haemophilus influenzae

<400> SEQUENCE: 19
agattggaaa gaaacacaag aaaaaga                                        27

<210> SEQ ID NO 20
<211> LENGTH: 23
<212> TYPE: DNA
<213> ORGANISM: Haemophilus influenzae

<400> SEQUENCE: 20
caccatcggc atatttaacc act                                            23

<210> SEQ ID NO 21
<211> LENGTH: 37
<212> TYPE: DNA
<213> ORGANISM: Haemophilus influenzae

<400> SEQUENCE: 21
aaacatccaa tcgtaattat agtttaccca ataaccc                             37

<210> SEQ ID NO 22
<211> LENGTH: 23
<212> TYPE: DNA
<213> ORGANISM: Haemophilus influenzae

<400> SEQUENCE: 22
ggttaaatat gccgatggtg ttg                                            23

<210> SEQ ID NO 23
<211> LENGTH: 21
<212> TYPE: DNA
<213> ORGANISM: Haemophilus influenzae

<400> SEQUENCE: 23
tgcatcttta cgcacggtgt a                                              21

<210> SEQ ID NO 24
<211> LENGTH: 33
<212> TYPE: DNA
<213> ORGANISM: Haemophilus influenzae

```
<400> SEQUENCE: 24
ttgtgtacac tccgttggta aagaacttg cac                                  33

<210> SEQ ID NO 25
<211> LENGTH: 19
<212> TYPE: DNA
<213> ORGANISM: Haemophilus influenzae

<400> SEQUENCE: 25
cctctggtgt cttacctgc                                                 19

<210> SEQ ID NO 26
<211> LENGTH: 21
<212> TYPE: DNA
<213> ORGANISM: Haemophilus influenzae

<400> SEQUENCE: 26
gcatcggctt gaccatattt c                                              21

<210> SEQ ID NO 27
<211> LENGTH: 24
<212> TYPE: DNA
<213> ORGANISM: Haemophilus influenzae

<400> SEQUENCE: 27
actttagccc tttctttatt agca                                           24

<210> SEQ ID NO 28
<211> LENGTH: 24
<212> TYPE: DNA
<213> ORGANISM: Haemophilus influenzae

<400> SEQUENCE: 28
cttttaagaa ttccacgcca gtat                                           24

<210> SEQ ID NO 29
<211> LENGTH: 24
<212> TYPE: DNA
<213> ORGANISM: Haemophilus influenzae

<400> SEQUENCE: 29
tttcagcagc aatatcttta ccat                                           24

<210> SEQ ID NO 30
<211> LENGTH: 24
<212> TYPE: DNA
<213> ORGANISM: Haemophilus influenzae

<400> SEQUENCE: 30
tatccaaggc ttagaaaaat ccac                                           24
```

SELECTIVE DETECTION OF HAEMOPHILUS INFLUENZAE

CROSS REFERENCE TO RELATED APPLICATIONS

This application is a divisional of U.S. patent application Ser. No. 13/996,913 filed Jun. 21, 2013, which is a U.S. National Phase of international application PCT/US12/22753 filed Jan. 26, 2012 and which claims priority to and depends from U.S. Provisional Application No. 61/436,535 filed Jan. 26, 2011, the entire contents of each of which are incorporated herein by reference.

GOVERNMENT INTEREST

The invention described herein may be manufactured, used, and licensed by or for the United States Government.

FIELD OF THE INVENTION

This invention relates generally to processes for detection of foreign organisms in fluid samples. More specifically, the invention relates to selective detection of *Haemophilus influenzae* in biological or other fluid media. Processes are described for rapid and sensitive detection of *Haemophilus influenzae* in human and animal biological samples and quantification thereof. Diagnostic kits are provided for detection of *Haemophilus influenzae* in a clinical, laboratory, or field setting.

BACKGROUND OF THE INVENTION

*Haemophilus influenzae* (Hi) is a gram-negative coccobacillus of the family Pasturellaceae responsible for several, often life-threatening, respiratory infections including meningitis. Its sole niche is the human respiratory tract, where it can be asymptomatically carried.

Hi is serotyped based on 6 capsule types (designated a-f) or it can be non-typeable (NT). Hi is the etiologic agent of a wide variety of diseases, ranging from otitis media to sinusitis to septicemia to chronic obstructive pulmonary disease. The pathogenicity of Hi depends on the presence or absence of a capsule and the specific capsule type. The *Haemophilus* influenza serotype b (Hib) is responsible for most Hi disease in young children and for as much as 50% of adult diseases. Hib is the target of vaccines administered to infants. Widespread vaccination programs dramatically decreased the prevalence of disease in all countries employing the vaccines. Non-typeable Hi has, thus, become the most prevalent cause of Hi related infections in the United States.

Common techniques employed for the identification of Hi serotypes include slide agglutination serotyping (SAST) and the polymerase chain reaction (PCR). The reading and scoring of SAST results are subjective, and can be difficult to interpret if an agglutination reaction is weak or if there is variability in the sensitivity or specificity of commercially available serotyping reagents.

The change in prevalence of disease causing primary serotypes underscores the need for continued monitoring to detect serotype replacement or identify vaccine failure. Thus, there is a need for compositions and methods useful in improving the detection and serotyping of *Haemophilus influenzae*.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

Processes and material are provided for the detection of the presence or absence of *Haemophilus influenzae* in a sample. A process illustratively includes producing an amplification product by amplifying a *Haemophilus influenzae* nucleotide sequence using a forward primer that hybridizes to a first region within a gene of *Haemophilus influenzae*, and a reverse primer that hybridizes to a second region within said gene, where the gene is hpd, acsB, bcsB, ccsD, dcsE, ecsH, or Hif bexD, under conditions suitable for a polymerase chain reaction. The amplification product is detected to identify *Haemophilus influenzae* in the sample. A probe is optionally used to measure the process of detecting the presence or absence of *Haemophilus influenzae* in a sample. Detection of *Haemophilus influenzae* in a sample can be used in the diagnosis or treatment of infection in a subject.

A forward primer optionally includes SEQ ID NO: 1, SEQ ID NO: 4, SEQ ID NO: 7, SEQ ID NO: 10, SEQ ID NO: 13, SEQ ID NO: 16, SEQ ID NO: 19, or SEQ ID NO: 22, a variant thereof, an analog thereof, or a derivative thereof. A reverse primer optionally includes SEQ ID NO: 2, SEQ ID NO: 5, SEQ ID NO: 8, SEQ ID NO: 11, SEQ ID NO: 14, SEQ ID NO: 17, SEQ ID NO: 20, or SEQ ID NO: 23, a variant thereof, an analog thereof, or a derivative thereof. A probe is optionally SEQ ID NO: 3, SEQ ID NO: 6, SEQ ID NO: 9, SEQ ID NO: 12, SEQ ID NO: 15, SEQ ID NO: 18, SEQ ID NO: 21, or SEQ ID NO: 24, a variant thereof, an analog thereof; or a derivative thereof.

One or more controls are optionally analyzed. Optionally, the first detection signal is compared to a second detection signal, wherein the second detection signal results from detection of a complementary amplification product produced from a control sample. Optionally, the complementary amplification product is generated by PCR amplification of a purified *Haemophilus influenzae*, or portion thereof, or from a nucleic acid calibrator. A second detection signal, or a third detection signal derived from a nucleic acid calibrator are optionally generated in parallel with the first detection signal. A nucleic acid calibrator is optionally extracted in parallel to said sample. A nucleic acid calibrator is optionally a known amount of *Haemophilus influenzae* nucleic acid sequence and a known amount of a medium similar to the sample.

Also provided is another process of detecting *Haemophilus influenzae* in a sample. A process illustratively includes producing a plurality of amplification products by combining the sample with a plurality of primer sets wherein each set is capable of hybridizing to a acsB, bcsB, ccsD, dcsE, ecsH, or Hif bexD nucleotide sequence under conditions suitable for a polymerase chain reaction, and determining the serotype of a *Haemophilus influenzae* in the sample by detecting at least one amplification product. The plurality of primer sets optionally includes a forward primer with the sequence of SEQ ID NO: 1, SEQ ID NO: 4, SEQ ID NO: 7, SEQ ID NO: 10, SEQ ID NO: 13, or SEQ ID NO: 16, and a reverse primer with the sequence of SEQ ID NO: 2, SEQ ID NO: 5, SEQ ID NO: 8, SEQ ID NO: 11, SEQ ID NO: 14, or SEQ ID NO: 17. Optionally a probe is used in the process. The probe optionally includes SEQ ID NO: 3, SEQ ID NO: 6, SEQ ID NO: 9, SEQ ID NO: 12, SEQ ID NO: 15, SEQ ID NO: 18, SEQ ID NO: 21, or SEQ ID NO: 24.

Also provided are kits for detecting *Haemophilus influenzae* infection in a sample. The kits include a forward primer with a sequence capable of hybridizing to a first portion of a *Haemophilus influenzae* gene, a reverse primer capable of hybridizing to a second portion of the gene, and optionally a non-degenerate probe. The genes are hpd, acsB, bcsB, ccsD, dcsE, ecsH, or Hif bexD. The probe optionally has the sequence SEQ ID NO: 3, SEQ ID NO: 6, SEQ ID NO: 9, SEQ ID NO: 12, SEQ ID NO: 15, SEQ ID NO: 18, SEQ ID NO: 21, or SEQ ID NO: 24.

Detection is optionally achieved by gel electrophoresis, Southern blotting, liquid chromatography, mass spectrometry, liquid chromatography/mass spectrometry, mass spectrometry, static fluorescence, dynamic fluorescence, high performance liquid chromatography, ultra-high performance liquid chromatography, enzyme-linked immunoadsorbent assay, real-time PCR, nucleotide sequencing, or combinations thereof.

Also provided for is a library of oligonucleotides for detecting and serotyping *Haemophilus influenzae* in a sample. The library comprises at least two isolated oligonucleotides each capable of hybridizing to a gene of *Haemophilus influenzae*, such as hpd, acsB, bcsB, ccsD, dcsE, ecsH, or Hif bexD. At least one of the oligonucleotides in the library has a sequence of any of SEQ ID NOs: 1-24, variants thereof, analogs thereof, or derivatives thereof.

BRIEF DESCRIPTION OF THE DRAWINGS

FIG. 1 is a schematic representation of capsule loci of and real-time PCR target genes of *Haemophilus influenzae* serotypes a, b, c, d, e, and f. Detection assay target genes are highlighted in boxes.

DETAILED DESCRIPTION OF EMBODIMENTS OF THE INVENTION

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the processes are described as an order of individual steps or using specific materials, it is appreciated that described steps or materials may be interchangeable such that the description of the invention includes multiple parts or steps arranged in many ways as is readily appreciated by one of skill in the art.

The invention has utility for the detection of *Haemophilus influenzae* (Hi) in a sample. Compositions are provided for the rapid and, optionally serotype specific, detection of Hi in clinical isolates or other biological or environmental samples. The compositions and methods of the invention provide rapid and direct detection of Hi that is both non-typeable (NT) and of a common a-f serotype. The inventions may use direct detection of the genes whose products produce Hi polysaccharide capsule types by identification of serotype specific sequences of the genes of the cap locus. The cap locus includes three functionally defined regions. Regions 1 and 3 are common to all Hi serotypes and encode proteins for the processing and transport of capsular material including bexABCD and hcsAB. Region 2 is unique among capsule types and encodes proteins responsible for capsule biosynthesis. The invention provides compositions and methods that specifically detect serotypes of Hi through molecular techniques related to the polymerase-chain reaction (PCR) directed to serotype specific nucleotide sequences.

Alone, or in addition to serotype specific detection, compositions and methods for pan detection of Hi are also provided. The surface exposed antigen, protein D, is conserved among all Hi strains. Protein D is a 42 kDa IgD binding protein of known sequence. The invention also provides new, specific, and robust compositions and methods for detecting the presence or absence of Hi in a sample by rapidly detecting the presence of protein D. When combined with the serotype specific assays, a process of inexpensive and rapid screening and serotype specific detection is achieved.

Compositions and methods are provided for the sensitive detection of Hi in samples, such as biological or environmental samples, using techniques involving PCR. Primers and probes are provided that amplify and detect the presence or absence of genes *Haemophilus* influenza protein D (hpd), *Haemophilus influenzae* serotype a capsule synthesis B (acsB), *Haemophilus influenzae* serotype b capsule synthesis B (bcsB), *Haemophilus influenzae* serotype c capsule synthesis D (ccsD), *Haemophilus influenzae* serotype d capsule synthesis E (dcsE), *Haemophilus influenzae* serotype e capsule synthesis H (ecsH), *Haemophilus influenzae* serotype f export D (bexD), or related mRNA with high specificity and broad Hi recognition that are subsequently detectable in sensitive detection systems.

The following definitional terms are used throughout the specification without regard to placement relative to these terms.

As used herein, the term "variant" defines either a naturally occurring genetic mutant of Hi or a recombinantly prepared variation of Hi, or any portion thereof, each of which contain one or more mutations in its hpd, acsB, bcsB, ccsD, dcsE, ecsH, and Hif bexD genes compared to the sequence of one or more of Genbank accession numbers: CP000671, M37487, L12445, and GQ401998 through GQ402009 (hpd); acsB: Z37516.2; bcsB: AF549213.1; ccsD: HM770876; dcsE: HM770877; ecsH: HM770878; Hif bexD: AF549211.1. The term "variant" may also refer to either a naturally occurring variation of a given peptide or a recombinantly prepared variation of a given peptide or protein in which one or more amino acid residues have been modified by amino acid substitution, addition, or deletion.

As used herein, the term "analog" in the context of a non-proteinaceous analog defines a second organic or inorganic molecule that possesses a similar or identical function as a first organic or inorganic molecule and is structurally similar to the first organic or inorganic molecule. An analog optionally includes a conservative alteration of one nucleotide for another nucleotide. A conservative alteration is one that will result in no amino acid change, or an amino acid change for an amino acid with similar properties (e.g. hydrophobic, hydrophilic, etc.). An analog optionally maintains an identical or similar G/C ratio. An analog is optionally a substitution of a purine for a purine or a pyrimidine for a pyrimidine.

As used herein, the term "derivative" in the context of a non-proteinaceous derivative defines a second organic or inorganic molecule that is formed based upon the structure of a first organic or inorganic molecule. A derivative of an organic molecule includes, but is not limited to, a molecule modified, e.g., by the addition or deletion of a hydroxyl, methyl, ethyl, carboxyl or amine group. An organic molecule may also be esterified, alkylated and/or phosphorylated. A derivative is also defined as a degenerate base mimicking a C/T mix such as that from Glen Research Corporation, Sterling, Va., illustratively LNA-dA or LNA-dT, or other nucleotide modification known in the art or otherwise.

As used herein, the term "mutant" defines the presence of one or more mutations in the nucleotide sequence of an organism as compared to a wild-type organism.

As used herein, the term "hybridizes under stringent conditions" describes conditions for hybridization and washing under which nucleotide sequences having at least 30%, 35%, 40%, 45%, 50%, 55%, 60%, 65%, 70%, 75%, 80%, 85%, 90%, or 95% base pair matches to each other typically remain hybridized to each other. Such hybridization conditions are described in, for example but not limited to, Current Protocols in Molecular Biology, John Wiley & Sons, N.Y. (1989), 6.3.1-6.3.6; Basic Methods in Molecular Biology, Elsevier Science Publishing Co., Inc., N.Y. (1986), pp. 75-78, and 84-87; and Molecular Cloning, Cold Spring Harbor Laboratory, N.Y. (1982), pp. 387-389, and are well known to those skilled in the art. A non-limiting example of stringent hybridization conditions is hybridization at 55° C. in water or aqueous buffer.

An "isolated" or "purified" nucleotide or oligonucleotide sequence is substantially free of cellular material or other contaminating proteins from the cell or tissue source from which the nucleotide is derived, or is substantially free of chemical precursors or other chemicals when chemically synthesized. The language "substantially free of cellular material" includes preparations of a nucleotide/oligonucleotide in which the nucleotide/oligonucleotide is separated from cellular components of the cells from which it is isolated or produced. Thus, a nucleotide/oligonucleotide that is substantially free of cellular material includes preparations of the nucleotide having less than about 30%, 20%, 10%, 5%, 2.5%, or 1% (by dry weight) of contaminating material. When a nucleotide/oligonucleotide is produced by chemical synthesis, it is optionally substantially free of chemical precursors or other chemicals, i.e., it is separated from chemical precursors or other chemicals that are involved in the synthesis of the molecule. Accordingly, such preparations of the nucleotide/oligonucleotide have less than about 30%, 20%, 10%, or 5% (by dry weight) of chemical precursors or compounds other than the nucleotide/oligonucleotide of interest. In some embodiments of the present invention, a nucleotide/oligonucleotide is isolated or purified.

As used herein, the term sample is a portion of a larger source material. A sample is optionally a solid, gaseous, or fluidic sample. A sample is illustratively an environmental or biological sample. An environmental sample is illustratively, but not limited to, water, sewage, soil, or air. A "biological sample" is a sample obtained from a biological organism, a tissue, cell, cell culture medium, or any medium suitable for mimicking one or more biological conditions. Non-limiting examples include saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, vitreal fluid, nasal secretions, throat or nasal materials. In some embodiments, target agents are contained in: CSF; serum; whole blood; throat fluid; or nasopharyngeal fluid or other respiratory fluid.

As used herein, the term "medium" refers to any liquid or fluid sample in the presence or absence of a bacterium. A medium is illustratively a solid sample that has been suspended, solubilized, or otherwise combined with fluid to form a fluidic sample. Non-limiting examples include buffered saline solution, cell culture medium, acetonitrile, trifluoroacetic acid, any other fluid recognized in the art as suitable for combination with bacteria or other cells, or for dilution of a biological sample or amplification product for analysis, or combinations thereof.

To determine the percent identity of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences (i.e., % identity=number of identical overlapping positions/total number of positions multiplied by 100%). In some embodiments, the two sequences are the same length.

The determination of percent identity between two sequences can also be accomplished using a mathematical algorithm. A non-limiting example of a mathematical algorithm utilized for the comparison of two sequences is the algorithm of Karlin and Altschul, 1990, Proceedings of the National Academy of Sciences, 87:2264-2268, modified as in Karlin and Altschul, 1993, Proceedings of the National Academy of Sciences, 90:5873-5877. Such an algorithm is incorporated into the NBLAST and XBLAST programs of Altschul, S. F., et al., 1990, Journal of Molecular Biology 215:403-410. BLAST nucleotide searches are performed with the NBLAST nucleotide program parameters set, e.g., for score=100, word length=12 to obtain nucleotide sequences homologous to nucleic acid molecules of the present invention. BLAST protein searches are performed with the XBLAST program parameters set, e.g., to score 50, word length=3 to obtain amino acid sequences homologous to a protein molecule of the present invention. To obtain gapped alignments for comparison purposes, Gapped BLAST are utilized as described in Altschul et al., 1997, Nucleic Acids Research, 25:3389-3402. Alternatively, PSI BLAST is used to perform an iterated search that detects distant relationships between molecules (Id.). When utilizing BLAST, Gapped BLAST, and PSI Blast programs, the default parameters of the respective programs (e.g., of XBLAST and NBLAST) are used (see, e.g., http://blast.ncbi.nlm.nih.gov/). Another non-limiting example of a mathematical algorithm utilized for the comparison of sequences is the algorithm of Myers and Miller, 1988, Computer Applications in the Biosciences, 4:11-17. Such an algorithm is incorporated in the ALIGN program (version 2.0), which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described above, with or without allowing gaps. In calculating percent identity, typically only exact matches are counted.

As used herein, the terms "subject" and "patient" are synonymous and refer to a human or non-human animal, optionally a mammal including non-primates such as cows, pigs, horses, goats, sheep, cats, dogs, avian species and rodents; a non-human primate such as monkeys, chimpanzees, and apes; and a human, also denoted specifically as a "human subject". It is appreciated that a subject is optionally a cell, tissue, or organ.

Processes are described that provide rapid, specific, and sensitive detection of Hi in one or more samples by amplifying one or more nucleotide sequences of the hpd, acsB, bcsB, ccsD, dcsE, ecsH, and Hif bexD genes by processes similar to the polymerase chain reaction (PCR). The hpd, acsB, bcsB, ccsD, dcsE, ecsH, and Hif bexD genes are described herein as target genes. As such, the term "target" is directed to one or more of Hi hpd, acsB, bcsB, ccsD, dcsE, ecsH, Hif bexD genetic DNA sequences or mRNA sequences.

An oligonucleotide forward primer with a nucleotide sequence complementary to a unique sequence in an hpd, acsB, bcsB, ccsD, dcsE, ecsH, or Hif bexD nucleotide sequence, or mRNA sequence of these genes, is hybridized to its complementary sequence and extended. Similarly, a reverse oligonucleotide primer complementary to a second strand of hpd, acsB, bcsB, ccsD, dcsE, ecsH, or Hif bexD DNA in the same or an alternate region is hybridized and extended. This system allows for amplification of specific nucleic acid sequences and is suitable for simultaneous or sequential detection systems. It is appreciated that while the description is generally directed to sequences of the hpd, acsB, bcsB, ccsD, dcsE, ecsH, and Hif bexD genes, or a Hi consensus sequence thereof, that mRNA encoding at least a portion of any of these encoded proteins is equally detectable by the processes and compositions of the inventions.

The present invention relates to the use of the sequence information of Hi for diagnostic processes. In particular, the present invention provides a process for detecting the presence or absence of nucleic acid molecules of Hi, natural or artificial variants, analogs, or derivatives thereof, in a sample. Processes involve obtaining a biological sample from one or more of various sources and contacting the sample with a compound or an agent capable of detecting a nucleic acid sequence of hpd, acsB, bcsB, ccsD, dcsE, ecsH, or Hif bexD, natural or artificial variants, analogs, or derivatives thereof, such that the presence of Hi, natural or artificial variants, analogs, or derivatives thereof, is detected in the sample. In some embodiments, the presence of Hi, natural or artificial variants, analogs, or derivatives thereof, is detected in the sample by a real-time polymerase chain reaction (RT-PCR) using the primers that are constructed based on a partial nucleotide sequence of the Hi organism. In a non-limiting embodiment, forward and reverse primers are listed in Table 1.

TABLE 1

| Target Gene | Oligo Designation | 5' to 3' Nucleotide Sequence |
|---|---|---|
| acsB | acs2Fwd261 | GGT CTG CGG TGT CCT GTG T (SEQ ID NO: 1) |
|  | acs2Rev427 | CCG GTC ATC TTT TAT GCT CCA A (SEQ ID NO: 2) |
|  | acs2Pb375[2] | (FAM)-TAA TTT TCT TGC "T"CA ATA CCG CCT TCC CA-(SpC6) (SEQ ID NO: 3) |
| bcsB | bcs2Fwd192 | TGA TGC ATT GAA AGA AGG TGT AAT TT (SEQ ID NO: 4) |
|  | bcs2Rev359 | CCT GCG GTA ATA ACA TGA TCA TAA A (SEQ ID NO: 5) |
|  | bcs2Pb244 | (FAM)-TG TCG TGC AGT AGC AAA CCG TAA CCT TAC TC-(BHQ1) (SEQ ID NO: 6) |
| ccsD | HicFwd7667 | CAT TGG TGA TGG TTC AGT TAT TGG (SEQ ID NO: 7) |
|  | HicRev7784 | TAC AGC ATT CAG CAA TAA TGG G (SEQ ID NO: 8) |
|  | HicPb7726[2] | (FAM)-ATT GCA "T"CG CCG CAG GAG TTC CCG -(SpC6) (SEQ ID NO: 9) |
| dcsE | HidFwd2211 | CCT AAA ATA CGG ACC TAG TGC AC (SEQ ID NO: 10) |
|  | HidRev2255 | CCG ATG AGA CCA AGT ATG GTT A (SEQ ID NO: 11) |
|  | HidPb2221 | (FAM)-AAC GAG C"T"A GAG CTG GTG CTG AA-(SpC6) (SEQ ID NO: 12) |
| ecsH | HieFwd1523 | ACT AAA ATA TGG CCC AAA CCC AC (SEQ ID NO: 13) |
|  | HieRev1589 | CCG ATG AGC CCA AGT ATG ATG A (SEQ ID NO: 14) |
|  | HiePb1555[2] | (FAM)-AAC GAG CAA AAG CCG G"T"G CGG AT-(SpC6) (SEQ ID NO: 15) |
| Hif bexD | Hif bexDFwd7164 | 5' CCC TGA AAA GCG TTG ACT TTG 3' (SEQ ID NO: 16) |
|  | Hif bexDRev7313 | 5' CCA ACT TCA GGA CCA AGT CAT TC 3' (SEQ ID NO: 17) |
|  | Hif bexDPb7242[2] | 5'(FAM)-TGC TGC TAA C"T"C AGA TGC ATC AGC TCC TT-(SpC6)3 (SEQ ID NO: 18) |
| hpd #1 | hpdF729 | 5' AGATTGGAAAGAAACACAAGAAAAAGA 3' (SEQ ID NO: 19) |
|  | hpdR819 | 5' CACCATCGGCATATTTAACCACT 3' (SEQ ID NO: 20) |
|  | hpdPbr762i | 5' (FAM)-AAACATCCAATCG"T"AATTATAGTTTACCCAATAACCC-(SpC6) 3' (SEQ ID NO: 21) |
| hpd #3 | hpdF822 | 5' GGTTAAATATGCCGATGGTGTTG 3' (SEQ ID NO: 22) |
|  | hpdR952 | 5' TGCATCTTTACGCACGTGTA 3' (SEQ ID NO: 23) |
|  | hpdPb896i | 5' (FAM)-TTGTGTACACTCCGT"T"GGTAAAGAACTTGCAC-(SpC6) 3' (SEQ ID NO: 24) |

[1]All primers and probes were synthesized at the CDC Biotechnology Core Facility.
[2]"T" is conjugated to BHQ1.

In Table 1, the labels and quenchers are presented for illustrative purposes alone and are not a limitation on the nucleotide sequences.

In some embodiments primer sets are used for the detection or serotyping of a Hi in a sample. A primer set is defined as two sequentially different primers that hybridize with a gene of Hi at different positions such that an amplification product is produced under conditions of a polymerase chain reaction. A primer set is illustratively operable to amplify at least a portion of a Hi gene that is hpd, acsB, bcsB, ccsD, dcsE, ecsH, or Hif bexD. In some embodiments, a primer set includes the forward and reverse primers of each gene as listed in Table 1.

In some embodiments, a primer or a probe includes a variant, analog, or derivative of any sequence provided herein. As such, a primer or probe is optionally a variant, analog, or derivative of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or any combination thereof. Unless otherwise specified, a primer or probe includes a variant, analog, or derivative thereof. Optionally, a primer or probe does not include a variant, analog, or derivative of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or any combination thereof.

The processes, compositions, and kits of the invention optionally include a plurality of primers, probes, primer sets, or combinations thereof. Illustratively, a single detection and serotyping reaction uses plurality of primers that will allow simultaneous detection and serotyping of Hi in a sample. In some embodiments a library of primers, probes, or combinations thereof are provided with this capability. Optionally, a library includes primers suitable to amplify a sequence of a gene or mRNA of Hi hpd, acsB, bcsB, ccsD, dcsE, ecsH, or Hif bexD, or combinations thereof, or any fraction thereof.

It is further appreciated that a set of amplification reactions are optionally performed to first detect the presence or absence of Hi in a sample, and subsequently, prior to, or simultaneous with determine the serotype of any Hi organisms present in the sample. In some embodiments, detection of Hi is performed using primers and/or probes suitable to detect the presence of the hpd gene or mRNA sequence in the sample. Serotyping is optionally performed by using a plurality of primers and probes for the simultaneous, sequential, or other detection of any serotype of Hi. Optionally, the primers and probes for serotyping include primers suitable to amplify, and optionally a probe suitable to detect an amplification product of, a sequence of a gene or mRNA of Hi hpd, acsB, bcsB, ccsD, dcsE, ecsH, or Hif bexD, or combinations thereof, or any fraction thereof. Some embodiments of the invention use primers, and optionally probes, to detect all of a sequence of a gene or mRNA of Hi that is hpd, acsB, bcsB, ccsD, dcsE, ecsH, or Hif bexD. Should the primers and optional probes used to detect the presence of an oligonucleotide sequence of acsB, bcsB, ccsD, dcsE, ecsH, or Hif bexD all be negative, a positive signal with the hpd primers and optional probe(s) will indicate the presence of NT-Hi (non-typeable).

An agent for detecting Hi nucleic acid sequences is a labeled nucleic acid probe capable of hybridizing thereto or to one or more amplification products. In some embodiments, the nucleic acid probe is a nucleic acid molecule comprising or consisting of the nucleic acid sequence of SEQ ID NOs: 3, 6, 9, 12, 15, 18, 21, or 24, which sufficiently specifically hybridizes under stringent conditions to a Hi nucleic acid sequence. A probe is optionally labeled with a fluorescent molecule, illustratively a fluorescein (PAM) molecule, and a quencher, illustratively the black hole quencher BHQ1.

Processes optionally involve a real-time quantitative PCR assay. In some embodiments, the quantitative PCR used in the present invention is the TaqMan assay (Holland et al., 1991, Proceedings of the National Academy of Sciences 88(16):7276-7280). It is appreciated that the processes are amenable to performance on other RT-PCR systems and protocols that use alternative reagents illustratively including, but not limited to Molecular Beacons probes, Scorpion probes, multiple reporters for multiplex PCR, combinations thereof, or other DNA detection systems.

The assays are performed on an instrument designed to perform such assays, for example those available from Applied Biosystems (Foster City, Calif.). In some embodiments, the present invention provides a real-time quantitative PCR assay to detect the presence of Hi, natural or artificial variants, analogs, or derivatives thereof, in a biological sample by subjecting the Hi nucleic acid from the sample to PCR reactions using specific primers, and optionally detecting the amplified product using a probe. In some embodiments, the probe is a TaqMan probe which consists of an oligonucleotide with a 5'-reporter dye and a 3'-quencher dye.

As one example, a fluorescent reporter dye, such as FAM dye (illustratively 6-carboxyfluorescein), is covalently linked optionally to the 5' end of the oligonucleotide probe. Other dyes illustratively include TAMRA, AlexaFluor dyes such as AlexaFluor 495 or 590, Cascade Blue, Marina Blue, Pacific Blue, Oregon Green, Rhodamine, Fluoroscein, TET, HEX, Cy5, Cy3, and Tetramethylrhodamine. Each of the reporters is quenched by a dye or other non-fluorescent quencher, optionally at the 3' end. Quenching molecules are suitably matched to the fluorescence maximum of the dye. Any suitable fluorescent probe for use in real-time PCR (RT-PCR) detection systems is illustratively operable in the instant invention. Similarly, any quenching molecule for use in RT-PCR systems is illustratively operable. In some embodiments, a 6-carboxyfluorescein reporter dye is present at the 5'-end and matched to BLACK HOLE QUENCHER (BHQ1 (4'-(2-Nitro-4-toluyldiazo)-2'-methoxy-5'-methylazobenzene-4"-(N-ethyl)-N-ethyl-2-cyanoethyl-(N,N-diisopropyl)-phosphoramidite), Biosearch Technologies, Inc., Novato, Calif.) The fluorescence signals from these reactions are captured at the end of extension steps as PCR product is generated over a range of the thermal cycles, thereby allowing the quantitative determination of the bacterial load in the sample based on an amplification plot.

The Hi nucleic acid sequences are optionally amplified simultaneously with or prior to being detected. The term "amplified" defines the process of making multiple copies of the nucleic acid from a single or lower copy number of a nucleic acid sequence molecule. The amplification of nucleic acid sequences is carried out in vitro by biochemical processes known to those of skill in the art. The amplification agent may be any compound or system that will function to accomplish the synthesis of primer extension products, including enzymes. Suitable enzymes for this purpose include, for example, E. coli DNA polymerase I, Taq polymerase, Klenow fragment of E. coli DNA polymerase I, T4 DNA polymerase, AmpliTaq Gold DNA Polymerase from Applied Biosystems, other available DNA polymerases, reverse transcriptase (preferably iScript RNase H+ reverse transcriptase), ligase, and other enzymes, including heat-stable enzymes (i.e., those enzymes that perform primer extension after being subjected to temperatures sufficiently elevated to cause denaturation). In some embodiments, the enzyme is hot-start iTaq DNA polymerase from Bio-rad (Hercules, Calif.). Suitable enzymes will facilitate combination of the nucleotides in the proper manner to form the primer extension products that are complementary to each mutant nucleotide strand. Generally, the synthesis is initiated at the 3'-end of each primer and proceeds in the 5'-direction along the template strand, until synthesis terminates, producing molecules of different lengths. There may be amplification agents, however, which initiate synthesis at the 5'-end and proceed in the other direction, using the same process as described above. In any event, the processes of the invention are not to be limited to the embodiments of amplification described herein.

One process of in vitro amplification, which is used according to this invention, is the polymerase chain reaction (PCR) generally described in U.S. Pat. Nos. 4,683,202 and 4,683,195. The term "polymerase chain reaction" refers to a process for amplifying a DNA base sequence using a heat-stable DNA polymerase and two oligonucleotide primers, one complementary to the (+)-strand at one end of the sequence to be amplified and the other complementary to the (−)-strand at the other end. Because the newly synthesized DNA strands can subsequently serve as additional templates for the same primer sequences, successive rounds of primer annealing, strand elongation, and dissociation produce rapid and highly specific amplification of the desired sequence. Many polymerase chain reaction processes are known to those of skill in the art and may be used in the process of the invention. For example, DNA is subjected to 30 to 35 cycles of amplification in a thermocycler as follows: 2 minutes at 50° C., 10 minutes at 95° C., and then 50× (15 seconds at 95° C. plus 1 minute at 60° C.).

The primers for use in amplifying the mRNA or genomic DNA of Hi may be prepared using any suitable process, such as conventional phosphotriester and phosphodiester processes or automated embodiments thereof so long as the primers are capable of hybridizing to the nucleic acid sequences of interest. One process for synthesizing oligonucleotides on a modified solid support is described in U.S. Pat. No. 4,458,066. The exact length of the primer will depend on many factors, including temperature, buffer, and nucleotide composition. The primer must prime the synthesis of extension products in the presence of the inducing agent for amplification.

Primers used according to the processes of the invention are complementary to each strand of nucleotide sequence to be amplified. The term "complementary" means that the primers hybridize with their respective strands under conditions that allow the agent for polymerization to function. In other words, the primers that are complementary to the flanking sequences hybridize with the flanking sequences and permit amplification of the nucleotide sequence. Optionally, the 3' terminus of the primer that is extended is perfectly base paired with the complementary flanking strand. Probes optionally possess nucleotide sequences complementary to one or both strands of the hpd, acsB, bcsB, ccsD, dcsE, ecsH, or Hif bexD genes of Hi. Optionally, primers contain the nucleotide sequences of SEQ ID NOs: 1, 2, 4, 5, 7, 8, 10, 11, 13, 14, 16, 17, 19, 20, 22, or 23. It is appreciated that the complements of SEQ ID NOs: 1, 2, 4, 5, 7, 8, 10, 11, 13, 14, 16, 17, 19, 20, 22, or 23 are similarly suitable for use in the instant invention. It is further appreciated that oligonucleotide sequences that hybridize with SEQ ID NOs: 1, 2, 4, 5, 7, 8, 10, 11, 13, 14, 16, 17, 19, 20, 22, or 23 are also similarly suitable. Finally, multiple positions are available for hybridization on the hpd, acsB, bcsB, ccsD, dcsE, ecsH, or Hif bexD genes and these positions will be also suitable hybridization with a probe when used with the proper forward and reverse primers.

Those of ordinary skill in the art will know of various amplification processes that can also be utilized to increase the copy number of target Hi nucleic acid sequence. The nucleic acid sequences detected in the process of the invention are optionally further evaluated, detected, cloned, sequenced, and the like, either in solution or after binding to a solid support, by any process usually applied to the detection of a specific nucleic acid sequence such as another polymerase chain reaction, oligomer restriction (Saiki et al., 1985, BioTechnology, 3:1008-1012), allele-specific oligonucleotide (ASO) probe analysis (Conner et al., 1983, Proceedings of the National Academy of Sciences 80:278-282), oligonucleotide ligation assays (OLAs) (Landegren et al., 1988, Science, 241:1077-1080), RNase Protection Assay and the like. Molecular techniques for DNA analysis have been reviewed (Landegren et al., 1988, Science, 242:229-237). Following DNA amplification, the reaction product may be detected by Southern blot analysis, with or without radioactive probes. In such a process, for example, a small sample of DNA containing the nucleic acid sequence obtained from the tissue or subject is amplified, and analyzed via a Southern blotting technique. The use of non-radioactive probes or labels is facilitated by the high level of the amplified signal. In some embodiments of the invention, one nucleoside triphosphate is radioactively labeled, thereby allowing direct visualization of the amplification product by autoradiography. In some embodiments, amplification primers are fluorescently labeled and run through an electrophoresis system. Visualization of amplified products is by light detection followed by computer assisted graphic display, without a radioactive signal.

Methods of detecting amplified oligonucleotides illustratively include gel electrophoresis, mass spectrometry, liquid chromatography, fluorescence, luminescence, gel mobility shift assay, fluorescence resonance energy transfer, nucleotide sequencing, enzyme-linked immunoadsorbent assay, chromatography illustratively affinity chromatography, immunoenzymatic methods (Ortiz, A. and Ritter, E., 1996, Nucleic Acids Research, 24:3280-3281), streptavidin-conjugated enzymes, DNA branch migration (Lishanski, A., et al., 2000, Nucleic Acids Research, 28(9):e42), enzyme digestion (U.S. Pat. No. 5,580,730), colorimetric methods (Lee, K., 2003, Biotechnology Letters, 25:1739-1742), or combinations thereof.

The term "labeled" with regard to the probe is intended to encompass direct labeling of the probe by coupling (i.e., covalently linking) a detectable substance to the probe, as well as indirect labeling of the probe by reactivity with another reagent that is directly labeled. Examples of indirect labeling include detection of a probe using a fluorescently labeled antibody and end-labeling or central labeling of a DNA probe with biotin such that it can be detected with fluorescently labeled streptavidin. The detection method of the invention can be used to detect DNA, RNA, or genomic nucleic acids in a sample in vitro as well as in vivo. For example, in vitro techniques for detection of nucleic acids include northern hybridizations, in situ hybridizations, reverse transcriptase-PCR, real-time-PCR, and DNase protection. In vivo techniques for detection of Hi include introducing into a subject organism a labeled antibody directed against a polypeptide component or directed against a particular nucleic acid sequence of Hi. For example, the antibody can be labeled with a radioactive marker whose presence and location in the subject organism can be detected by standard imaging techniques, including autoradiography.

The size of the primers used to amplify a portion of the nucleic acid sequence of Hi is at least 5, and often 10, 15, 20, 25, or 30 nucleotides in length. Optionally, the GC ratio, the relative amount of G and C in the primer, is above 30%, 35%, 40%, 45%, 50%, 55%, or 60% so as to prevent hair-pin structures on the primer. The amplicon is optionally of sufficient length to be detected by standard molecular biology methodologies. The forward primer is optionally shorter than the reverse primer or vice versa. Techniques for modifying the melting temperature ($T_m$) of either primer are operable herein. An illustrative forward primer contains LNA-dA and LNA-dT (Glen Research Corporation, Sterling, Va.) so as to match the $T_m$ with a corresponding alternate primer.

An inventive process uses a polymerization reaction that employs a nucleic acid polymerizing enzyme, illustratively a DNA polymerase, RNA polymerase, reverse transcriptase, or mixtures thereof. It is further appreciated that accessory proteins or molecules are present to form the replication machinery. A polymerizing enzyme is optionally a thermostable polymerase or thermodegradable polymerase. Use of thermostable polymerases is well known in the art, for example, Taq polymerase, which is available from Invitrogen Corporation. Thermostable polymerases allow a polymerization reaction to be initiated or ended by changing the temperature or other conditions in the reaction mixture without destroying the activity of the polymerase.

Accuracy of the base pairing of DNA sequence during amplification is provided by the specificity of the enzyme. Error rates for Taq polymerase tend to be false base incorporation of $10^{-5}$ or less. (Johnson, Annual Reviews of Biochemistry, 1993, 62:685-713; Kunkel, 1992, Journal of Biological Chemistry, 267:18251-18254). Specific examples of thermostable polymerases illustratively include those isolated from *Thermus aquaticus*, *Thermus thermophilus*, *Pyrococcus woesei*, *Pyrococcus furiosus*, *Thermococcus litoralis* and *Thermotoga maritima*. Thermodegradable polymerases illustratively include *E. coli* DNA polymerase, the Klenow fragment of *E. coli* DNA polymerase, T4 DNA polymerase, T7 DNA polymerase and other examples known in the art. It is recognized in the art that other polymerizing enzymes are similarly suitable. Illustrative examples include *E. coli*, T7, T3, SP6 RNA polymerases and AMV, M-MLV, and HIV reverse transcriptases.

A polymerase is optionally bound to a primer. When the Hi gene sequence is a single-stranded DNA molecule due to heat denaturing, the polymerase is bound at the primed end of the single-stranded nucleic acid at an origin of replication. A binding site for a suitable polymerase is optionally created by an accessory protein or by any primed single-stranded nucleic acid.

In some embodiments, detection of PCR products of the Hi nucleic acid sequence is achieved by mass spectrometry. Mass spectrometry has several advantages over real-time PCR systems in that it can be used to simultaneously detect the presence of Hi and decipher mutations in target nucleic acid sequences allowing identification and monitoring of emerging strains. Further, mass spectrometers are prevalent in clinical laboratories. Similar to fluorescence based detection systems, mass spectrometry is capable of simultaneously detecting multiple amplification products and provide a multiplexed and controlled approach to accurately quantify components of biological or environmental samples.

Multiple mass spectrometry platforms are suitable for use in the invention illustratively including matrix assisted laser desorption ionization time of flight mass spectrometry (MALDI-TOF), electrospray mass spectrometry, electrospray ionization-Fourier transform ion cyclotron resonance mass spectrometry (ESI-FTICR), multi-stage mass spectrometry fragmentation analysis (MS/MS), mass spectrometry coupled with liquid chromatography such as high performance liquid chromatography mass spectrometry (HPLC) and ultra performance liquid chromatography isotope dilution tandem mass spectrometry (UPLC-ID/MS/MS), and variations thereof.

It is appreciated that numerous other detection processes are similarly suitable for measuring an amplification product by detecting a detection signal. Illustrative examples include, but are not limited to, liquid chromatography, mass spectrometry, liquid chromatography/mass spectrometry, static fluorescence, dynamic fluorescence, high performance liquid chromatography, ultra-high performance liquid chromatography, enzyme-linked immunoadsorbent assay, real-time PCR (RT-PCR), gel electrophoresis, or combinations thereof.

Optionally, PCR amplification products are generated using complementary forward and reverse oligonucleotide primers. In a non-limiting example, Hi genetic sequences or fragments thereof are amplified by the primer pairs: SEQ ID NOs: 1 and 2 that amplify a conserved sequence in the acsB gene producing a 188 nucleotide amplicon; SEQ ID NOs: 4 and 5 that amplify a conserved sequence in the bcsB gene producing a 192 nucleotide amplicon, SEQ ID NOs: 7 and 8 that amplify a conserved sequence in the ccsD gene producing a 139 nucleotide amplicon; SEQ ID NOs: 10 and 11 that amplify a conserved sequence in the dcsE gene producing a 66 nucleotide amplicon; SEQ ID NOs: 13 and 14 that amplify a conserved sequence in the ecsH gene producing a 88 nucleotide amplicon; SEQ ID NOs: 16 and 17 that amplify a conserved sequence in the Hif bexD gene producing a 172 nucleotide amplicon; or SEQ ID NOs: 19 and 20, or 22 and 23 that are useful to amplify a conserved sequence in the hpd gene producing a 113 or 151 nucleotide amplicon, respectively. The resulting amplification product is either directly detected using a probe, or is subsequently processed and prepared for detection by one or more processes known in the art. It is appreciated that the complements of SEQ ID NOs: 1, 2, 4, 5, 7, 8, 10, 11, 13, 14, 16, 17, 19, 20, 22, and 23 are similarly suitable for use in the invention. It is further appreciated that oligonucleotide sequences that hybridize with SEQ ID NOs: 1, 2, 4, 5, 7, 8, 10, 11, 13, 14, 16, 17, 19, 20, 22, and 23 are also similarly suitable. Finally, multiple positions are available for hybridization on the Hi genome and a target nucleic acid sequence and will be also suitable hybridization with forward and reverse primers that may or may not be used with a probe for real-time PCR.

Multiple amplification products are optionally simultaneously produced in a PCR reaction that is then available for simultaneous detection and quantification. Thus, multiple detection signals are inherently produced or emitted that are separately and uniquely detected in one or more detection systems. It is appreciated that multiple detection signals are optionally produced in parallel. Optionally, a single biological sample is subjected to analysis for the simultaneous or sequential detection of Hi target sequences. It is appreciated that three or more independent or overlapping sequences are simultaneously or sequentially measured in the inventive process. Oligonucleotide matched primers (illustratively SEQ ID NOs 1 and 2, or any other primer set of Table 1) are simultaneously or sequentially added and the biological sample, or a portion thereof, is subjected to proper thermocycling reaction parameters. For detection by mass spectrometry, a single sample of the amplification products from each target is simultaneously analyzed allowing for rapid and accurate determination of the presence of and optionally the serotype of Hi. Optionally, analysis by real-time PCR is employed capitalizing on multiple probes with unique fluorescent signatures. Thus, each gene is detected without interference by other amplification products. This multi-target approach increases confidence in quantification and provides for additional internal control.

In some embodiments, the processes further involve obtaining a control sample from a control subject, contacting the control sample with a compound or agent capable of detecting the presence of Hi nucleic acid in the sample, and comparing the presence or absence of mRNA or genomic DNA in the control sample with the presence of mRNA or genomic DNA in the test sample.

The invention also encompasses kits for detecting the presence of Hi nucleic acids in a test sample. The kit, for example, includes a labeled compound or agent capable of detecting a nucleic acid molecule in a test sample and, in certain embodiments, for determining the quantity of Hi in the sample.

For oligonucleotide-based kits, the kit includes, for example: (1) an oligonucleotide, e.g., a detectably labeled oligonucleotide, which hybridizes to a nucleic acid sequence of Hi and/or (2) a pair of primers (one forward and one reverse) useful for amplifying a nucleic acid molecule containing at least a portion of the Hi sequence such as a target sequence. The kit can also include, e.g., a buffering agent, a preservative, or a protein stabilizing agent. The kit can also include components necessary for detecting the detectable agent (e.g., an enzyme or a substrate). The kit can also contain a control sample or a series of control samples that are assayed and compared to the test sample contained. Each component of the kit is optionally enclosed within an individual container and all of the various containers are optionally enclosed within a single package along with instructions for use.

The instant inventive processes are amenable to use for diagnosis and, therefore, to inform treatment of Hi infection in a subject capable of infection or transfection by or with Hi.

To increase confidence and to serve as an internal or external control, a purified solution containing one or more serotypes of Hi is used as a biological sample. By amplification of a single sample with known quantities of one or more serotypes of Hi or of a set of samples representing a titration of one or more serotypes of Hi, and comparison with the detected amplification product, the level of Hi in the unknown biological sample is determined. Optionally, the purified and quantified Hi solution is analyzed in parallel with the unknown sample to reduce inter assay error or to serve as a standard curve for quantitation of unknown Hi in the biological sample. Using purified and quantified Hi solution provides for a similar complete genetic base DNA strand for amplification.

In some embodiments, a subgenomic fragment is cloned into a plasmid for amplification, purification, and used as a quantitative comparator or nucleic acid calibrator. In a non-limiting example, a DNA subgenomic fragment of one or more targets is optionally amplified from a positive nasal swab using primers bracketing the target sequences. It is appreciated that other sequences are similarly suitable for use as a quantitative control. The known concentration of the subgenomic fragment is used to create a standard curve for quantitative determinations and to access amplification efficiency.

Also provided is a kit for detecting Hi infection that contains reagents for the amplification, or direct detection of Hi or portions thereof. An exemplary kit illustratively includes a forward and reverse primer pair, and a non-degenerate probe. In some embodiments, the forward and reverse primers have the oligonucleotide sequence SEQ ID NOs 1 and 2 and a nondegenerate probe of the sequence SEQ ID NO 3. Primer and probe sets for any target such as the target sets listed in Table 1 are similarly suitable. It is appreciated that a diagnostic kit optionally contains primers and probes that are the complements of SEQ ID NOs 1-24 or that hybridize with oligonucleotides SEQ ID NOs 1-24. It is further appreciated that a diagnostic kit optionally includes ancillary reagents such as buffers, solvents, thermostable polymerases, nucleotides, and other reagents necessary and recognized in the art for amplification and detection of Hi in a biological sample.

A kit for detection of Hi infection in a patient optionally contains reagents for PCR based detection of Hi target sequences, either structural or non-structural, and optionally for detection of antibodies directed to Hi proteins. The components of the kits are any of the reagents described above or other necessary and non-necessary reagents known in the art for solubilization, detection, washing, storage, or other need for a diagnostic assay kit.

Various aspects of the present invention are illustrated by the following non-limiting examples. The examples are for illustrative purposes and are not a limitation on any practice of the present invention. It will be understood that variations and modifications can be made without departing from the spirit and scope of the invention. Reagents illustrated herein are commercially available, and a person of ordinary skill in the art readily understands where such reagents may be obtained.

EXAMPLES

Example 1: Preparation of DNA from Clinical Isolates

The clinical isolates tested in this study are submitted to the Meningitis Laboratory at the Centers for Disease Control and Prevention (CDC) through Active Bacterial Core Surveillance (ABCs) or routine surveillance as described by Mothershed, E. A., et al., 2004, Journal of Clinical Microbiology, 42:320-28. Bacterial strains include ATCC strains, clinical invasive isolates and carriage isolates. Clinical invasive isolates are collected as part of the Active Bacterial Core surveillance of the Centers for Disease Control and Prevention's Emerging Infectious Program (http://www.cdc.gov/abcs/index.htm). This population and laboratory-based surveillance system includes 10 states: California (3 San Francisco Bay area counties), Colorado (5 Denver area counties), Connecticut, Georgia, Maryland, Minnesota, New York (15 Albany and Rochester area counties), Oregon, Tennessee (11 urban counties) and New Mexico. Carriage isolates of Hi and *Haemophilus haemolyticus* are collected during a Hi carriage survey in Minnesota from February to May of 2009 (Lowther et al., Epidemiol Infect. 2011 May 18:1-9. [Epub ahead of print], PMID: 21676359). The clinical and carriage isolates in this study are characterized using standard microbiology and molecular biology methods. All strains are grown on Chocolate II Agar supplemented with hemoglobin and IsoVitalex (Becton, Dickinson and Company, Sparks, Md.) in a 5% $CO_2$ incubator at 37° C. for 18-24 hours. Seventeen invasive isolates are chosen for sequencing hpd. These isolates include one each of Hi a-f, four NT-Hi, one *Haemophilus aphrophilus* (proposed to be classified as *Aggregatibacter aphrophilus*) (Norskov-Lauritsen and Kilian, 2006, International Journal of Systemic and Evolutionary Microbiology, 56:2135-2146), one *H. haemo-*

*lyticus*, one *Haemophilus paraphrophilus* (proposed to be classified as *Aggregatibacter aphrophilus*) (Norskov-Lauritsen and Kilian, 2006, International Journal of Systemic and Evolutionary Microbiology, 56:2135-2146), and four *Haemophilus parainfluenzae*.

Genomic DNA is prepared for use in the various steps of assay design and optimization by DNA extraction from isolates or CSFs as described previously (Carvalho et al., 2007, Journal of Clinical Microbiology, 45:2460-2466). DNA is purified using the QIAamp DNA Mini Kit (QIAGEN, Valencia, Calif.) by Protocol C then quantified for use in standard curve experiments using a NanoDrop ND-1000 spectrophotometer (NanoDrop Technologies, Wilmington, Del.). Boiled cell lysates for assay validation are prepared using standard methods.

Example 2: PCR and Sequencing of Hic, Hid, and Hie Region II and Hpd

Sequencing templates are prepared by conventional PCR. For sequencing of Hic, Hid, and Hie the forward primer HiBexDR3 (5' CCT CTG GTG TCT TAC CTG C 3' (SEQ ID NO: 25)) and reverse primer HiHcsAR3 (5' GCA TCG GCT TGA CCA TAT TTC 3' (SEQ ID NO: 26)) are used. Sequencing of hpd is performed using forward primer hpdF13 (5' ACTTTAGCCCTTTCTTTATTAGCA 3' (SEQ ID NO: 27)) or hpdR557-seq (5' TTTCAGCAG-CAATATCTTTACCAT 3' (SEQ ID NO: 29)) and reverse primers hpdR1061 (5' CTTTTAAGAATTCCACGCCAG-TAT 3' (SEQ ID NO: 28)) or hpdF474-seq (5' TATC-CAAGGCTTAGAAAAATCCAC 3' (SEQ ID NO: 30)). Thermocycler parameters are 4 minutes at 94° C.; 10× (1 minute at 94° C., 1 minute at 55° C., 8 minutes at 68° C.); 20× (1 minute at 94° C., 1 minute at 55° C., 8 minutes+5 seconds per round at 68° C.); 8 minutes at 68° C.; 4° C. indefinite hold. The master mix includes the following reagents for a 25.5-µL total reaction volume per reaction: 20.25 µL sterile PCR grade water (Roche Diagnostics, Indianapolis, Ind.); 2.5 µL Expand High Fidelity Buffer (10×) with $MgCl_2$ (Roche Diagnostics GmbH, Mannheim, Germany); 0.5 µL PCR Nucleotide Mix at 10 mM each dNTP (Roche Diagnostics GmbH); 0.5 of a 20 µM working stock of the forward primer; 0.5 µL of a 20 µM working stock of the reverse primer; 0.25 µL Expand High Fidelity Enzyme Mix (Roche Diagnostics GmbH); and 1 µL (60-150 ng) template DNA.

Sequencing templates are first purified from the PCR reactants using the QIAquick PCR Purification Kit (QIAGEN, Valencia, Calif.), eluting the products in sterile PCR grade water (Roche Diagnostics, Indianapolis, Ind.). For automated dye-terminator nucleotide cycle sequencing, the BigDye Terminator v3.1 Cycle Sequencing Kit (Applied Biosystems, Foster City, Calif.) is used per the manufacturer's instructions, adding 2-3 µL (120-300 ng) of template DNA and 1 µL of 3.2 µM primer per sequencing reaction.

Sequencing reaction products are purified using the DyeEx 2.0 Spin Kit (QIAGEN, Valencia, Calif.) and separated and detected with an ABI PRISM 3130xl Genetic Analyzer (Applied Biosystems, Carlsbad, Calif.). Sequences were analyzed with the Lasergene DNAStar v. 7 Program SeqMan. Open reading frames (orfs) are predicted using Sequin Application Version 9.20. Sequence homologies are determined using the Basic Local Alignment Search Tool protein blast (BLASTp).

Example 3: Primer and Probe Design

All primer walking and sequencing primers are designed by hand. For RT-PCR primer and probe design, a consensus sequence of each target gene is generated using SeqMan and target gene sequences generated from Hi of each respective serotype. Each consensus sequence is entered into Primer Express Software for RT-PCR Version 3.0 (Applied Biosystems, Carlsbad, Calif.), with the default parameters for TaqMan quantification changed to maximum probe length of 35 nt, and minimum and maximum amplified region lengths of 150 and 300 nt, respectively.

Example 4: Assay Characteristics

A Stratagene Mx3005P real-time (quantitative) PCR machine (Stratagene, La Jolla, Calif.) is used. To optimize the primers, 2× QuantiTect SYBR Green RT-PCR Master Mix from the QuantiTect SYBR Green RT-PCR Kit (QIAGEN, Valencia, Calif.) is used. Primers are tested in triplicate or quadruplicate at final concentrations of 100, 300, 600, and 900 nM, where forward and reverse primers are tested at each combination of concentrations. To determine the optimal concentration of the probe, probes are tested in triplicate at final concentrations of 50, 100, 200, 300, and 400 nM. Cycle parameters are 2 minutes at 50° C.; 10 minutes at 95° C.; 50× (15 seconds at 95° C., 1 minute at 60° C.). For probe optimization and subsequent experiments, including standard curve and sensitivity and specificity determination, the master mix includes the following reagents for a 25-pt total reaction volume per reaction: 4.5 µL sterile PCR grade water (Roche Diagnostics, Indianapolis, Ind.); 12.5 µL TaqMan 2× PCR Master Mix (Applied Biosystems, Carlsbad, Calif.); 2 µL of a working stock of the forward primer; 2 µL of a working stock of the reverse primer; 2 µL probe; and 2 µL template DNA. $C_t$ values ≤35 are considered positive; $C_t$s in the range of 36-40 equivocal; and $C_t$ values >40 are considered negative.

Final concentrations of primers and probes listed in Table 1 are: acs2Fwd261-100 nM; acs2Rev427-300 nM, acs2PB375-100 nM; bsc2Fwd192-300 nM; bcs2Rev359-600 nM; bsc2Pb244-100 nM; HicFwd7667-600 nM; HicRev7784-300 nM; HicPb7726-200 nM; HidFwd2211-600 nM; HidRev2255-100 nM; HidPb2221-300 nM; HieFwd1523-600 nM; HieRev1589-600 nM; HiePb1555-200 nM; HifbexDFwd7164-600 nM; HifbexDRev7313-300 nM; HifbexDPb7242-200 nM; hpdF729-300 nM; hpdR819-100 nM; hpdPbr762i-200 nM; hpdF822-100 nM; hpdR952-300 nM; and hpdPb896i-100 nM. It is appreciated that the labels and quenchers present on several nucleotides of the sequences of Table 1 are for illustrative purposes only and are not meant to be a limitation thereon.

A specificity panel of serotyped Hi organisms is tested using the above primer and probe concentrations to determine whether any cross-reactivity with other bacterial organisms is observed. Examination of acsB (Hia), bcsB (Hib), ccsD (Hic), dcsE (Hid), ecsH (Hie), and bexD (Hif) of the serotype-specific capsule biosynthesis or export operons demonstrate 100% serotype specificity when tested against panels of Hi isolates of the respective serotype according to slide agglutination serotyping as illustrated in Table 2.

TABLE 2

| | No. PCR negative/No. tested (% Specificity) | | | | | |
|---|---|---|---|---|---|---|
| Serotype | acsB | bcsB | ccsD | dcsE | ecsH | Hif bexD |
| a | — | 63/63 | 63/63 | 63/63 | 63/63 | 63/63 |
| b | 49/49 | — | 49/49 | 49/49 | 49/49 | 49/49 |
| c | 21/21 | 21/21 | — | 21/21 | 21/21 | 21/21 |

TABLE 2-continued

| | No. PCR negative/No. tested (% Specificity) | | | | | |
|---|---|---|---|---|---|---|
| Serotype | acsB | bcsB | ccsD | dcsE | ecsH | Hif bexD |
| d | 15/15 | 15/15 | 15/15 | — | 15/15 | 15/15 |
| e | 61/61 | 61/61 | 61/61 | 61/61 | — | 61/61 |
| f | 60/60 | 60/60 | 60/60 | 60/60 | 60/60 | — |
| NT | 117/117 | 117/117 | 117/117 | 117/117 | 117/117 | 117/117 |
| Total | 323/323 (100%) | 337/337 (100%) | 365/365 (100%) | 371/371 (100%) | 325/325 (100%) | 326/326 (100%) |

The panel of known serotype Hi isolates is examined for the ability of the hpd assays to detect Hi and compared to other detection targets previously examined. The hpd #1 and #3 (protein D) assays detect 97% (229/237) and 99% (234/237) of Hi isolates respectively demonstrating that both assays are superior to prior molecular detection targets ompP2 and bexA (Table 3). The hpd assays detect isolates of all six Hi serotypes and NT-Hi.

TABLE 3

Real-time PCR Assays for Detection of Hi Isolates.

| Hi serotype | No. of isolates tested | No. of positives (positive rate %) | | | |
|---|---|---|---|---|---|
| | | hpd #1 | hpd #3 | ompP2 | bexA |
| a | 26 | 26 (100) | 26 (100) | 26 (100) | 21 (81) |
| b | 25 | 25 (100) | 25 (100) | 24 (96) | 23 (92) |
| c | 16 | 15 (94) | 16 (100) | 16 (100) | 10 (63) |
| d | 12 | 12 (100) | 12 (100) | 10 (83) | 5 (42) |
| e | 32 | 29 (91) | 32 (100) | 32 (100) | 0 |
| f | 24 | 24 (100) | 23 (96) | 24 (100) | 0 |
| NT | 102 | 98 (96) | 100 (98) | 87 (85) | 0 |
| Total | 237 | 229 (97) | 234 (99) | 219 (92) | 59 (25) |

A panel of non-Hi organisms is tested for specificity of the assays. The serotype specific assays demonstrate excellent specificity for Hi illustrating no cross-reactivity for any other organism tested (Table 4).

TABLE 4

| Organism | No. Isolates Tested | Real-time PCR Result | | | | | |
|---|---|---|---|---|---|---|---|
| | | acsB | bcsB | ccsD | dcsE | ecsH | Hif bexD |
| H. aphrophilus | 1 | — | — | — | — | — | — |
| H. parainfluenzae | 9 | — | — | — | — | — | — |
| H. haemolyticus | 2 | — | — | — | — | — | — |
| N. meningitidis A | 1 | — | — | — | — | — | — |
| N. meningitidis B | 2 | — | — | — | — | — | — |
| N. meningitidis C | 1 | — | — | — | — | — | — |
| N. meningitidis W135 | 2 | — | — | — | — | — | — |
| N. meningitidis X | 1 | — | — | — | — | — | — |
| N. meningitidis Y | 3 | — | — | — | — | — | — |
| N. meningitidis Z | 2 | — | — | — | — | — | — |
| N. meningitidis 29E | 1 | — | — | — | — | — | — |
| N. meningitidis nongroupable | 2 | — | — | — | — | — | — |
| N. cinerea | 2 | — | — | — | — | — | — |
| N. gonorrhoeae | 2 | — | — | — | — | — | — |
| N. subflava | 1 | — | — | — | — | — | — |
| N. sicca | 1 | — | — | — | — | — | — |
| N. lactamica | 3 | — | — | — | — | — | — |
| N. polysaccharea/N. spp. | 2 | — | — | — | — | — | — |
| N. species | 5 | — | — | — | — | — | — |
| E. coli 07:K1(L) | 1 | — | — | — | — | — | — |
| E. coli 016:K1 (L) | 1 | — | — | — | — | — | — |
| Cryptococcus neoformans | 1 | — | — | — | — | — | — |

TABLE 4-continued

| Organism | No. Isolates Tested | acsB | bcsB | ccsD | dcsE | ecsH | Hif bexD |
|---|---|---|---|---|---|---|---|
| Moraxella catarrhalis | 7 | — | — | — | — | — | — |
| Staphylococcus aureus | 1 | — | — | — | — | — | — |
| Streptococus pneumoniae | 1 | — | — | — | — | — | — |
| Listeria monocytogenes | 1 | — | — | — | — | — | — |
| Actinobacillus pleuropneumoniae | 1 | — | — | — | — | — | — |
| Salmonella choleraesuis | 1 | — | — | — | — | — | — |
| Streptococcus agalactiae | 1 | — | — | — | — | — | — |
| Pseudomonas aeruginosa | 1 | — | — | — | — | — | — |
| Bordetella pertussis | 1 | — | — | — | — | — | — |
| Corynebacterium diphtheriae | 1 | — | — | — | — | — | — |
| Total, % Specificity | 62 | 100% | 100% | 100% | 100% | 100% | 100% |

To determine the Hi specificity of the hpd assays, a panel of 63 non-Hi isolates is tested using the hpd #1 and hpd #3 assays (Table 5). None of the non-Hi isolates tested are detected by the hpd #1 and bexA assays. Only two false positives are observed using the hpd #3 assay and the ompP2 assay.

TABLE 5

Non-Hi Bacterial Species Tested

| Organism | No. of isolates tested |
|---|---|
| Actinobacillus pleuropneumoniae | 1 |
| Branhamella catarrhalis | 1 |
| Cryptococcus neoformans | 1 |
| Escherichia coli O16:K1 (L) | 1 |
| Escherichia coli O7:K1(L) | 1 |
| Haemophilus aphrophilus[1] | 2 |
| Haemophilus haemolyticus | 16 |
| Haemophilus parainfluenzae | 5 |
| Haemophilus paraphrophilus[1] | 1 |
| Listeria monocytogenes | 1 |
| Neisseria cinerea | 2 |
| Neisseria gonorrhoeae | 1 |
| Neisseria lactamica | 11 |
| Neisseria meningitidis serogroup A, C, W135, X, Y, NG and 29E | 1 of each serogroup |
| Neisseria meningitidis serogroup B and Z | 2 of each serogroup |
| Neisseria sicca | 1 |
| Neisseria subflava | 1 |
| Pseudomonas aeruginosa | 1 |
| Salmonella choleraesuis | 1 |
| Staphylococcus aureus | 1 |
| Staphylococcus epidermidis | 1 |
| Streptococcus agalactiae | 1 |
| Streptococcus pneumoniae | 1 |
| Total | 63 |

[1]Both *H. aphrophilus* and *H. paraphrophilus* were proposed to be classified as *Aggregatibacter aphrophilus* (Norskov-Lauritsen and Kilian, 2006, International Journal of Systemic and Evolutionary Microbiology, 56: 2135-2146).

Assay detection limits are analyzed by titration of known levels of each Hi serotype. The assays detect 39 (Hia), 125 (Hib), 47 (Hic), 83(Hid), 59 (Hie), and 121 (Hif) copies per reaction of the Hi chromosome of the respective serotype. The assays are 90% (Hia), 90% (Hib), 88% (Hic), 95% (Hid), 94% (Hie), and 87% (Hif) efficient (Table 6).

TABLE 6

| Gene Target | For Detection of | Genomes Detected/Rxn at $C_t$ 35[1] | Rxn Efficiency[1] |
|---|---|---|---|
| acsB | H. influenzae a | 39 | 90% |
| bcsB | H. influenzae b | 125 | 90% |
| ccsD | H. influenzae c | 47 | 88% |
| dcsE | H. influenzae d | 83 | 95% |
| ecsH | H. influenzae e | 59 | 94% |
| Hif bexD | H. influenzae f | 121 | 87% |

[1]Average of results for 3-4 isolates.

For the hpd targets, the hpd #1 and hpd #3 assays consistently have lower LLD (lower limit of detection) than the bexA and ompP2 assays and were able to detect all Hi serotypes with comparable sensitivity (Table 7).

TABLE 7

Lower Limit of Detection of the Real-time PCR Assays[1]

| | Genome equivalents/PCR reaction | | | |
|---|---|---|---|---|
| Hi Serotype | hpd #1 | hpd #3 | ompP2 | bexA |
| a | 200 | 30 | 63000 | 130 |
| b | 580 | 59 | 31 | 139 |
| c | 91 | 14 | 330 | 181 |
| d | 430 | 44 | 99 | 351 |
| e | 240 | 23 | 67000 | ND[2] |
| f | 653 | 38 | 4925 | ND[2] |
| NT | 219 | 70 | 237 | ND[2] |
| Average | 345 | 40 | 19375 | 200 |

[1]the lower limit of detection is the DNA concentration yielding a Ct = 35.
[2]ND: not detected The hpd #3 assay has an average LLD (40 genomes/PCR reaction) nearly nine-fold lower than that of the hpd #1 assay (345 genomes/PCR reaction) under the tested conditions. The LLD of the ompP2 is much lower for Hib, Hic, Hid and NT-Hi than Hia, Hie and Hif (Table 7).

Example 5: Serotyping Clinical Isolates

The clinical isolates of Example 1 are tested for the ability of the serotype specific target assays to simultaneously identify and detect Hi serotypes in the isolates. Primers and probes of SEQ ID NOs: 1-18 directed to detection of acsB (Hia), bcsB (Hib), and bexD (Hif) ccsD (Hic), dcsE (Hid), ecsH (Hie), are combined in a single multiplex reaction chamber where the probes have distinguishable detection agents covalently bonded thereto. The same clinical isolates are tested with the multiplex approach. The results using the multiplex assay are identical to the results using the individual primer/probe set reactions.

For pan detection of Hi in clinical isolates, samples obtained from a prospective, active, hospital-based surveillance for bacterial meningitis in children from Ulaanbaatar, Mongolia aged 2 months to 5 years who were hospitalized for suspected meningitis are used. Suspected meningitis is defined as clinically suspected meningitis with at least one of the following: fever, headache, stiff neck, bulging fontanelle, or mental status change. Probable bacterial meningitis is defined as the presence of a white blood cell (WBC) count of ≥100 cells/mm$^3$ in CSF or turbid appearance of CSF (if the WBC count was not measured) if criteria for suspected meningitis are met. Confirmed bacterial meningitis in this study is defined as satisfied conditions of probable meningitis, and the isolation of Hi, *Neisseria meningitidis* (Nm) or *Streptococcus pneumoniae* (Sp) from CSF, detection of specific bacterial antigens in CSF by latex agglutination, or the isolation of bacterial pathogens from blood culture (Mendsaikhan et al., 2009, Clinical Infectious Diseases, 48 Supp; 1-2: S141-S146). A total of 111 CSF specimens are collected. Microbiological methods for identification of bacterial meningitis pathogens Hi, Nm and Sp are as described previously (Mendsaikhan et al., Clinical Infectious Diseases, 2009, 48 Supp; 1-2: S141-5146). The real-time PCR assays (the ctrA and lytA assays) are conducted to detect Nm and Sp, respectively (Mothershed et al., 2004, Journal of Clinical Microbiology, 42:320-328; Carvalho et al., 2007, Journal of Clinical Microbiology, 45:2460-2466).

The hpd #3 and bexA assays are used to detect Hi. Nm serogroup or Hi serotype of the confirmed cases is determined by slide agglutination or latex agglutination. If a CSF is positive for Nm or Hi by PCR only, the serogroup is determined by Nm serogroup-specific PCR assays (Mothershed et al., 2004, Journal of Clinical Microbiology, 42:320-328), or the serotype is determined by the bcsB PCR assay specific for Hib (Dolan et al., 2010, 110$^{th}$ ASM General Meeting, San Diego, Calif.). Corresponding pneumococcal serotypes within all Sp positive CSFs are determined by PCR assays as described at http://www.cdc.gov/ncidod/biotech/strep/pcr.htm (Carvalho et al., 2007, Journal of Clinical Microbiology, 45:2460-2466; Carvalho et al., 2010, Journal of Clinical Microbiology, 48:1611-1618). If a CSF is culture/latex negative but PCR positive for one of three bacterial species, additional PCR assays (serogroups-specific PCR assays for Nm, serotype-specific PCR assays for Sp, and the bcsB, ompP2 or bexA assay for Hi) are performed to detect the second target gene. The specimen is considered positive if the second target gene is detected. A total of 111 positive cases are detected.

Of the 111 suspected meningitis cases, 56 (50%) are confirmed by CSF culture, blood culture and/or latex agglutination (19 Hib, 24 Nm, and 13 Sp). The remaining 55 (50%) suspected but unconfirmed cases are negative for Nm, Hi, and Sp by culture and/or latex agglutination. Of the 56 CSFs from the confirmed meningitis cases, rt-PCR assays detect 100% (19/19) Hi, 88% (21/24) Nm and 100% (13/13) Sp (Table 8). rt-PCR results are consistent with culture and/or latex agglutination results, with the exception of one specimen that is Hib by slide agglutination and latex agglutination but serogroup B (NmB) by rt-PCR, and one specimen that is identified as NmB by latex agglutination but NmB and Hib by rt-PCR.

TABLE 8

Mongolia bacterial meningitis surveillance, 2004-7

| | CSF Culture and/or Latex positive (n = 56) | | | CSF Culture and Latex negative (n = 55) | | |
|---|---|---|---|---|---|---|
| | Hi | Nm | Sp | Hi | Nm | Sp |
| Total positive by culture and/or Latex Real-time PCR | 19 | 24 | 13 | 0 | 0 | 0 |
| hpd #3 | 19 | 11 | 0 | 8 | 0 | 0 |
| bexA | 19 | 11 | 0 | 7 | 0 | 0 |
| ctrA | 12 | 21 | 0 | 0 | 17 | 0 |
| lytA | 0 | 0 | 13 | 0 | 0 | 2 |
| CSF Culture | 15 | 10 | 8 | | | |
| Latex agglutination | 19 | 19 | 13 | | | |
| Blood culture | 9 | 7 | 4 | | | |

[1] This specimen was Nm by latex agglutination but NmB and Hib by rt-PCR.
[2] This specimen was Hib by culture and latex agglutination but NmB by rt-PCR.

Of the 55 CSFs from the suspected but unconfirmed meningitis cases, 45 cases meet the criteria for probable meningitis. Of these, there are 27 rt-PCR positives including 8 Hi (5 Hib and 3 non-b Hi), 17 Nm (6 NmA, 9 NmB and 2 NmW135) and 2 Sp (serotypes 18 and 6C). All these rt-PCR positive specimens are further confirmed by the presence of a second specific target gene. Among the 10 suspected meningitis cases that do not meet criteria for probable meningitis, none are positive by rt-PCR. rt-PCR assays improve overall detection of meningitis pathogens from 50% (56/111) to 75% (83/111). Two of the three non-b Hi specimens from the unconfirmed cases are positive for hpd, ompP2 and bexA. One non-b Hi specimen is positive for hpd and ompP2, but negative for bexA.

The hpd, bexA and lytA assays show good sensitivity when a composite reference standard or CSF culture standard is used (Table 9). The specificity of each rt-PCR assay is improved using the composite reference standard (Table 9), with a range of 72.9%-92.9% using the CSF culture standard compared to 80%-97.9% using the composite reference standard.

TABLE 9

| | Positive/total true positive | Sensitivity[1] (95% CI) | Negative/total true negative | Specificity (95% CI) |
|---|---|---|---|---|
| | | Culture standard Detection of Hi | | |
| bexA assay | 14/15 | 93.3% (68-100%) | 80/91 | 87.9% (79-94%) |
| hpd #3 assay | 14/15 | 93.3% (68-100%) | 79/91 | 86.8% (78-93%) |
| | | Detection of Nm | | |
| ctrA assay | 10/10 | 100% (69-100%) | 70/96 | 72.9% (63-81%) |
| | | Detection of Sp | | |
| lytA assay | 8/8 | 100% (63-100%) | 91/98 | 92.9% (86-97%) |
| | | Composite reference standard Detection of Hi | | |
| bexA assay | 18/19 | 94.7% (74-100%) | 83/90 | 92.2% (85-97%) |
| hpd #3 assay | 18/19 | 94.7% (74-100%) | 82/90 | 91.1% (83-96%) |
| | | Detection of Nm | | |
| ctrA assay | 21/24 | 87.5% (68-97%) | 68/85 | 80.0% (70-88%) |
| | | Detection of Sp | | |
| lytA assay | 13/13 | 100% (75-100%) | 94/96 | 97.9% (93-100%) |

Example 6: Detection of Hi Serotypes in Clinical Specimens

The ability of the assay of Example 4 using primers and probes of SEQ ID NOs: 1-18 directed to detection of acsB (Hia), bcsB (Hib), and bexD (Hif) ccsD (Hic), dcsE (Hid), ecsH (Hie) at the final concentrations indicated in Example 4. The primers and probes are combined in a single multiplex reaction chamber where the probes have distinguishable detection agents covalently bonded thereto as indicated in Table 1. Six serotype-specific assays as a whole panel to detect Hi are assessed and compared to culture and to hpd as the species-identifying target gene (Wang, X, et al., *Int J Med Microbiol*, 2011; 301:303-9) using DNA extractions of 21 hpd-positive Turkish CSF specimens. bcsB is positive for 17/21 (81.0%), acsB is positive for 1/21 (4.8%), and all six serotyping assays are negative for 3/21 (14.3%) specimens. Therefore, 18/21 (85.7%) specimens are Hi serotype positive (95% confidence interval [CI]: 65% to 96%) compared to 21/21 that were hpd-positive (100%). The $C_t$ values for the three hpd-positive, serotype-negative CSF extractions average 37.6 for bcsB while their hpd $C_t$ values average 34.0. Specimens for which any $C_t$ value is obtained for one serotype-specific assay yields no $C_t$ for the other 5 serotypes, correlating with the 100% serotype specificity of the assays found when they are tested on isolates.

Methods involving conventional biological techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; Current Protocols in Molecular Biology, ed. Ausubel et al., Greene Publishing and Wiley-Interscience, New York, 1992 (with periodic updates); and Short Protocols in Molecular Biology, ed. Ausubel et al., 52 ed., Wiley-Interscience, New York, 2002. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992.

Additional protocols such as PCR Protocols can be found in A Guide to Methods and Applications Academic Press, NY. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification," Methods in Enzymology vol. 182, and other volumes in this series; Current Protocols in Protein Science, John Wiley & Sons, New York, N.Y.; and manufacturer's literature on use of protein purification products known to those of skill in the art.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified. Methods of nucleotide amplification, cell transfection, and protein expression and purification are similarly within the level of skill in the art.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A process of determining presence or absence of *Haemophilus influenzae* in a sample comprising:
combining with the sample a first forward primer that hybridizes with a first portion and a first reverse primer that hybridizes with a second portion of *Haemophilus influenzae* hpd gene, under conditions suitable to produce a first amplification product by polymerase chain reaction (PCR), wherein the first forward primer comprises SEQ NO: 22 and the first reverse primer comprises SEQ ID NO: 23;
and
detecting the first amplification product to determine the presence or absence of *Haemophilus influenzae* in the sample using a first detectable probe comprising SEQ ID NO: 24.

2. The process of claim 1, wherein the detecting diagnoses *Haemophilus influenzae* infection in a subject.

3. The process of claim 1, further comprising producing and detecting a second amplification product, comprising:
amplifying a second *Haemophilus influenzae* nucleotide sequence using a second forward primer that hybridizes to a first region and a second reverse primer that hybridizes to a second region within acsB, bcsB, ccsD, dcsE, ecsH or Hif BexD gene of *Haemophilus influenza*, under conditions suitable to produce the second amplification product by PCR; and, detecting the presence or absence of said second amplification product to determine the presence or absence of *Haemophilus influenzae* in the sample.

4. The process of claim 3, wherein the second amplification product is produced subsequent to the first amplification product.

5. The process of claim 3, wherein the second forward primer comprises SEQ ID NO: 1, SEQ ID NO: 4, SEQ ID NO: 7, SEQ ID NO: 10, SEQ ID NO: 13 or SEQ ID NO: 16.

6. The process of claim 3, wherein the second reverse primer comprises SEQ ID NO: 2, SEQ ID NO: 5, SEQ ID NO: 8, SEQ ID NO: 11, SEQ ID NO: 14 or SEQ ID NO: 17.

7. The process of claim 3, wherein the detecting of the second amplification product is by a second detectable probe comprising SEQ ID NO: 3, SEQ ID NO: 6, SEQ ID NO: 9, SEQ ID NO: 12, SEQ ID NO: 15 or SEQ ID NO: 18.

8. The process of claim 1, wherein the first forward primer consists of SEQ ID NO: 22.

9. The process of claim 1, wherein the first reverse primer consists of SEQ ID NO: 23.

10. The process of claim 1, wherein the first probe comprises a fluorescent label.

11. The process of claim 1, wherein the first probe comprises a quencher.

12. A kit for detecting *Haemophilus influenzae* infection in a subject, comprising a first forward primer capable of hybridizing to a first portion of *Haemophilus influenza* hpd gene, a first reverse primer capable of hybridizing to a second portion of the *Haemophilus influenzae* hpd gene and a first probe comprising a detectable label and capable of hybridizing to a polymerase chain reaction (PCR) amplification product produced by the first primer and the second primer, wherein the first probe comprises SEQ ID NO: 24, the first forward primer comprises SEQ ID NO: 22, and the first reverse primer comprises SEQ ID NO: 23.

13. The kit of claim 12, wherein the first forward primer consists of SEQ ID NO: 22.

14. The kit of claim 12, wherein the first reverse primer consists of SEQ ID NO: 23.

15. The kit of claim 12, wherein the first probe comprises a fluorescent label.

16. The kit of claim 15, wherein the first probe further comprises a quencher.

17. The kit of claim 12, further comprising at least one second detectable probe comprising SEQ ID NO: 3, SEQ ID NO: 6, SEQ ID NO: 9, SEQ ID NO: 12, SEQ ID NO: 15 or SEQ ID NO: 18.

18. The kit of claim 12, further comprising at least one second forward primer comprising SEQ ID NO: 1, SEQ ID NO: 4, SEQ ID NO: 7, SEQ ID NO: 10, SEQ ID NO: 13 or SEQ ID NO: 16.

19. The kit of claim 12, further comprising at least one second reverse primer comprising SEQ ID NO: 2, SEQ ID NO: 5, SEQ ID NO: 8, SEQ ID NO: 11, SEQ ID NO: 14 or SEQ ID NO: 17.

* * * * *